United States Patent
Senn et al.

(10) Patent No.: US 7,119,515 B2
(45) Date of Patent: Oct. 10, 2006

(54) LIGHT POLYMERIZATION DEVICE

(75) Inventors: Bruno Senn, Buchs (CH); Wolfgang Plank, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 14 days.

(21) Appl. No.: 10/636,015

(22) Filed: Aug. 6, 2003

(65) Prior Publication Data

US 2004/0214138 A1  Oct. 28, 2004

(30) Foreign Application Priority Data

Apr. 25, 2003  (DE) ............................ P 103 19 010

(51) Int. Cl.
*H02J 7/00* (2006.01)
*A61C 3/00* (2006.01)

(52) U.S. Cl. .................................... 320/106; 433/141

(58) Field of Classification Search ............... 320/107, 320/110, 111, 112, 114, 115, 106, 126, 131, 320/125; 700/168; 439/540.1; 433/29, 433/141; 442/301
See application file for complete search history.

(56) References Cited

U.S. PATENT DOCUMENTS

| | | | | |
|---|---|---|---|---|
| 4,553,081 A | * | 11/1985 | Koenck | 320/131 |
| 5,471,129 A | | 11/1995 | Mann | 320/115 |
| 5,539,297 A | * | 7/1996 | Fiebig | 320/126 |
| 5,653,591 A | * | 8/1997 | Loge | 433/118 |
| 5,903,462 A | * | 5/1999 | Wagner et al. | 700/168 |
| 5,914,585 A | * | 6/1999 | Grabon | 320/125 |
| 5,947,729 A | * | 9/1999 | Bell | 433/98 |
| 6,068,474 A | * | 5/2000 | Senn et al. | 433/29 |
| 6,095,812 A | * | 8/2000 | Senn et al. | 433/29 |
| 6,104,162 A | * | 8/2000 | Sainsbury et al. | 320/111 |
| 6,175,211 B1 | * | 1/2001 | Brotto | 320/106 |
| 6,193,510 B1 | * | 2/2001 | Tsimerman | 433/29 |
| 6,218,806 B1 | * | 4/2001 | Brotto et al. | 320/106 |
| 6,561,845 B1 | * | 5/2003 | Ocheltree et al. | 439/540.1 |
| 6,602,074 B1 | * | 8/2003 | Suh et al. | 433/228.1 |
| 6,727,197 B1 | * | 4/2004 | Wilson et al. | 442/301 |

FOREIGN PATENT DOCUMENTS

| | | |
|---|---|---|
| DE | 41 16 604 A1 | 11/1992 |
| DE | 1470793 | * 10/2004 |
| IT | 993810 | * 10/1999 |

(Continued)

OTHER PUBLICATIONS

Smart Battery Data Specification and System Management Bus BIOS Interface Specification @ http://www.sbs-forum.org/specs/sbdat110.pdf, Benchmarq Electronics, Rev.1.1, Dec. 11, 1998, pp. 1-49.*

*Primary Examiner*—Pia Tibbits
(74) *Attorney, Agent, or Firm*—John C. Thompson; Alan S. Korman; Sandra J. Thompson

(57) ABSTRACT

A light polymerization device for polymerization of a polymerizable material includes a hand-held device having a multi-branch electrical supply receptacle or a multi-prong electrical supply plug for the connection of the hand-held device with the storage battery assembly or with a connection module, which, in particular, makes available a releasably connectable electrical supply connection as well as a data bus port or interface. A base station comprises a single receptacle or several receptacles for the receipt of the storage battery assembly. The base station can comprise an electrical supply plug connection via which the base station is supplied with electrical energy, especially electrical energy supplied via a power pack.

16 Claims, 3 Drawing Sheets

FOREIGN PATENT DOCUMENTS

| WO | WO 99/21505 | 5/1999 |
| WO | WO 01/60280 A1 | 8/2001 |

* cited by examiner

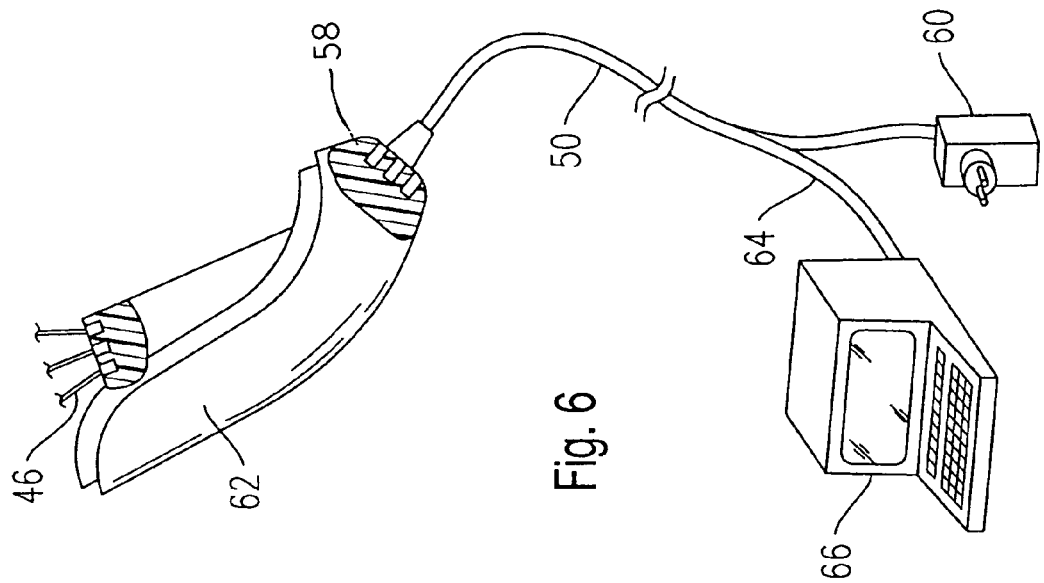
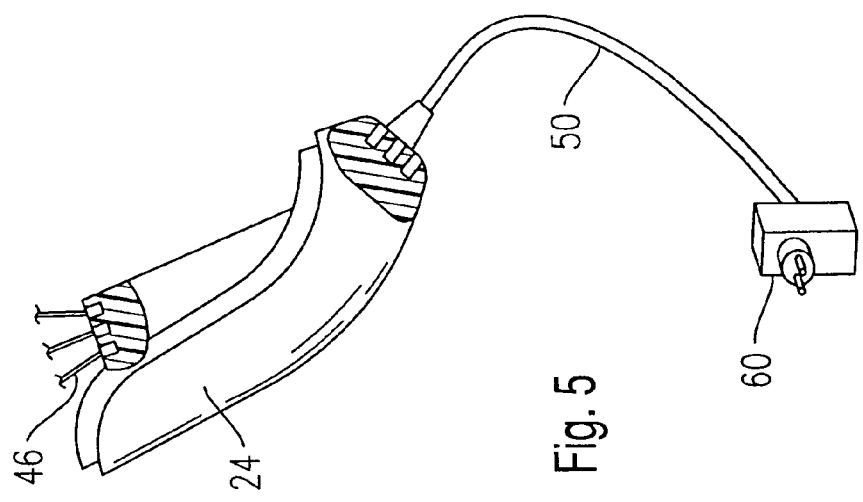
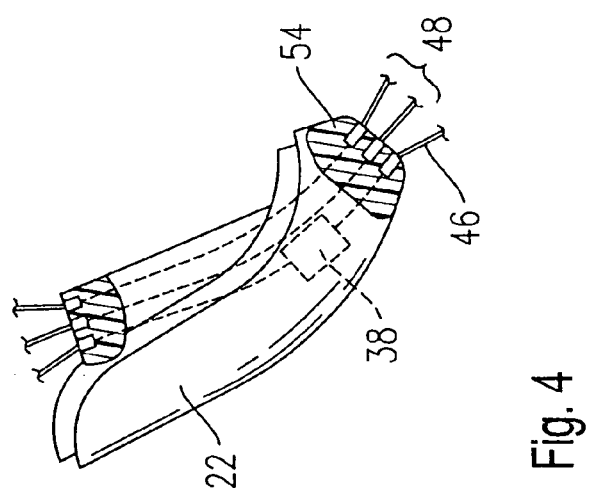

LIGHT POLYMERIZATION DEVICE

CROSS REFERENCE TO RELATED APPLICATIONS

This application claims foreign priority benefits under 35 U.S.C. §119 from German patent application Ser. No. 103 19 010.4 filed Apr. 25, 2003.

TECHNICAL FIELD

The present invention relates to a light polymerization device.

BACKGROUND OF THE INVENTION

Light polymerization devices had long been conventionally known as is disclosed, for example, in U.S. Pat. No. 5,471,129.

A light polymerization device of the above-noted type is provided with a storage battery assembly, which is mounted in the handgrip of a hand-held device. To effect the charging of the storage battery assembly, a base station is provided and the grip of the hand-held device is inserted into corresponding receptacles in the base station for a charging operation. To increase the convenience and availability of the device, two corresponding receptacles are provided so that two hand-held devices can be disposed in the same base station, whereupon one of the hand-held devices is loaded or charged and the other is available for use.

An approach of the above-noted type offers, in fact, a large degree of convenience and availability. However, due to the two required hand-held devices, such an approach is comparatively expensive.

Moreover, it has long been known, in connection with hand-held devices in other technical areas such as, for example, storage battery-powered or cordless drills or cordless screwdrivers, to couple together a storage battery assembly configured as a compact unit and a hand-held device into which the storage battery assembly can be inserted and, as required, to exchange or, respectively, to charge, solely the storage battery assembly.

Such approaches avoid the necessity of a separate hand-held device. On the one hand, it is known that the storage battery assemblies experience a diminution of their quality during the course of the operating time. In this connection, the so-called memory effect is part of this phenomenon but, as well, so is the effect, which occurs toward the end of the operational life, of increasing self-discharging of the storage battery assembly.

U.S. Pat. No. 5,471,129 discloses various measures to limit the negative effect of such disadvantages upon light polymerization devices, among which is the measure of monitoring the capacity of the storage battery assembly. The corresponding monitoring switch is mounted, in this approach, in the hand-held device. However, in connection with a spaced separation of the storage battery assembly and the hand-held device, monitoring a storage battery assembly in this manner, which is based upon acquisition of the storage battery assembly loading and discharging curves, is not possible or, at the least, is not practical, as even storage battery assemblies manufactured at the same time can possess different properties, which come to the fore upon deployment of the respective storage battery assembly.

One approach known in connection with digital film cameras for avoiding this undesired phenomenon is to provide the storage battery assembly itself with a microcontroller, which acquires the actual parameters of the storage battery assembly and the changes thereof during its operational life and stores such information.

A particular disadvantage of the entire range of such storage battery assemblies including, as well, high-value lithium ion storage battery assemblies, is their weight.

If a hand-held device is to be operated in a cable-free or cordless manner, the use of a storage battery assembly (or at least a battery pack) is, on the other hand, unavoidable.

Dentists, who seek a lightweight hand-held operation in connection with the use of a light polymerization device for polymerizing dental material, prefer, because of the weight of the storage battery assemblies, hand-held devices having an electrical energy supply cable connected with the base station. Such hand-held devices have, also, long been known, whereby, in the meantime, comparatively light yet nonetheless highly flexible cables can be provided. It is also known to use hand-held devices with a selectively deployable power pack connection and additionally, to outfit such hand-held devices for the possible receipt of a storage battery assembly.

A solution of this type is disclosed, for example, in DE 41 16 604. However, a hand-held device of this type is not particularly amenable to hand-held operation, if the storage battery assembly is, for the purpose of weight saving, removed from the hand-held device, as the hand-held device can no longer be readily deployed.

In considering the acquisition of operational parameters of the storage battery assembly, it is desirable, in connection with light polymerization devices, to also acquire the quality of the light output itself. In this connection, light sensors have been suggested which at least approximately acquire the outputted light performance and monitor the same.

On the other hand, the outputted light performance represents the most important quality criteria of a light polymerization device. The use of conventional halogen glow lamps causes vaporization of substantial portions of the tungsten layer or coating on the filament, whereupon the light performance decreases.

Once a storage battery assembly-powered light polymerization device has now been in relatively long use, the light performance decreases at a regular rate as does, as well, the capacity of the charge accumulator in the storage battery assembly. These performance opposing trends during the course of a storage battery assembly's usage reinforce the risk of an incomplete hardening of dental restoration pieces, comprised of synthetic materials, in the mouth of a patient. In this regard, monomers occasionally remain in such restoration pieces and follow-up demands against the dentist or, respectively, the manufacturer of the light polymerization device, cannot be excluded.

Moreover, the heretofore known solutions have not exhibited particularly good flexibility in connection with hand-held operations and fail to satisfy the various requirement profiles of the customers. Also, the reliability of the polymerization process leaves, in part, something to be desired.

OBJECTS AND SUMMARY OF THE INVENTION

The present invention provides a solution to the challenge of providing a light polymerization device which ensures, over its entire operational life, a constant light performance of the hand-held device, whereby the polymerization device has particularly good reliability while, nonetheless, making possible a flexible operation, as well, in connection with handling different requirement profiles.

In accordance with the present invention, an exchange of data and electricity is permitted in that there is provided a data bus having at least two connected modules such as, for example, a hand-held device a rechargeable battery storage assembly, and a data bus/electrical supply receptacle that may be integrated into a common connector. This opens multiple possibilities, even if the receptacle solely provides a single further contact for adding the capability of the data bus. For example, a micro-controller associated with a storage battery assembly can be informed that a higher performance is required by virtue of an increasingly reduced light output of the halogen light source, so that a timely counter measure can be implemented. Conversely, a micro-controller provided in the hand-held device can be informed that the load or charging condition of the storage battery assembly requires a re-charging of the storage battery assembly, whereby the hand-held device or, respectively, its micro-controller, can render a decision concerning a possible polymerization process based upon an improved decision base which takes into account the predetermined light irradiation time needed for hardening of the polymerizable material.

It is also possible, based upon the independently performed acquisition of parameters, to exchange various desired storage battery assemblies for one another and it is possible, for example, to provide a light polymerization device with two storage battery assemblies, one of which is charged and the other of which is available for operation. However, the respective available discharge capacity of the storage battery assembly can be supplied to the hand-held device.

In accordance with the present invention, it is especially advantageous that, as well, in connection with a power pack operation via a module, which is hereinafter designated as a "connection module", an easy and practical hand-held operation of the hand-held device is possible. The connection module is, in accordance with the present invention, advantageously configured in the same configuration as a storage battery assembly and comprises, on its lower end, a connection for a flexible cable, the flexible cable being in communication with the base station and making available the data bus while, however, also conducting the electrical energy supply to the hand-held device.

In this connection, three connectors (supply voltage, mass, and data bus) are sufficient, whereby the connectors for the data bus are preferably of a reduced connector cross-section of, for example, one-tenth to one-third of the connector cross-section of the supply voltage connector and are somewhat offset between these other connectors, so that the flexibility of the cable is not negatively influenced.

In accordance with the present invention, it is advantageous that a small three-pin plug can ensure the required connections. In connection with a connection of a plug connection to the connection module, the disposition of the plug in a triangular configuration at the same time provides a security measure against a defective plug-in connection.

In accordance with a further advantage of the present invention, the plug connections between the storage battery assembly and the hand-held device or, respectively, between the base station and the hand-held device or, respectively, between the service module and the hand-held device, can be configured in a covered and contact-protected manner. In this connection, a secure protection against corrosion is achieved without further measures and is ensured over several years, even with respect to a hand-held operation environment.

It is, moreover, particularly advantageous, in connection with the present invention, that the moveable module that is, the storage battery assembly, the connection module and/or the service module—are provided with two ports or interfaces, which provide the connection through to the data bus. In this manner, a bus-type arrangement is configured so that, therefore, transparent data can be conducted through the module as well.

An integrated port or interface, which is covered by the housing, is preferred while the other port or interface is preferably provided at the lower end and, as required, can likewise be covered.

Due to the provision of a data bus, the light measurement in the base station, for example, can easily be used to effect an automatic calibration of the hand-held device, whereupon the hand-held device can then, via its micro-controller, be configured with the corresponding required pre-set configuration. The micro-controller in the above-noted modules works together in a conventional manner with the other respective integrated components.

It is especially advantageous, in connection with the present invention, that a data exchange can still be realized in a desired manner via the inventive data bus even if only a portion of the possibly deployable modules is deployed. It is, for example, also possible to connect the data bus via a bus converter with a PC, which then offers the possibility of a data evaluation or a protocol run or, as well, the possibility of varying the basic pre-set configurations.

It is further particularly advantageous that, by the use of a micro-controller, the electronic components provided in the respective module are monitored by the micro-controller and controlled thereby. In this connection, at least one micro-controller is preferably provided in the hand-held device and at least one micro-controller is provided in the base station and, in a particularly favorable embodiment, a micro-controller is additionally provided in the storage battery assembly.

In accordance with a further advantageous embodiment of the present invention, it is provided that the hand-held device comprises a multi-branch electrical supply receptacle or a multi-prong or multi-pin electrical supply plug for the connection of the hand-held device with the storage battery assembly or with a connection module, which, in particular, makes available a releasably connectable electrical supply connection as well as a data bus port or interface.

In accordance with a further advantageous embodiment of the present invention, it is provided that the base station comprises a single receptacle or several receptacles for the receipt of the storage battery assembly. Moreover, the base station can comprise an electrical supply plug connection via which the base station is supplied with electrical energy, especially electrical energy supplied via a power pack. The electrical energy supply plug connection preferably comprises, as well, a bus contact, which is, in particular, integrated into the plug connection and via which, in particular in connection with a standard port or interface, the base station is connectable with a computer.

In accordance with yet a further advantageous embodiment of the present invention, it is provided that the connection of the computer to the service adapter extends via the base station and the data bus and, as well as, that the hand-held device is supportable on the base station and can be charged in a conventional manner, whereby the support of the hand-held device is effected, in particular, via a module disposed in or on the hand-held device.

In accordance with a further advantageous embodiment of the present invention, it is provided that the hand-held device, in the disposition thereof in which it is inserted into the base station, connects to plug contacts which connect to the data bus and which, in particular, connect the base station to the data bus via the module in the hand-held device.

In accordance with a further advantageous embodiment of the present invention, it is provided that, in connection with a storage battery assembly disposed in the hand-held device and a hand-held device inserted onto a base station, the connection module is insertable into a receptacle in the base station and thereby forms a connection to an external energy source including, in particular, to a power pack, or that, in connection with a storage battery assembly disposed in the hand-held device and a hand-held device inserted into the base station, the service module is insertable in a receptacle in the base station and forms thereby a connection to an external energy source including, in particular, a power pack.

Moreover, the plug connections for the connection of the module to the hand-held device and/or to the base station are preferably recessed and protected against contact.

Further advantages, details, and features are described in connection with the hereinafter following description of several embodiments of the present invention, with reference to the figures of the drawing.

BRIEF DESCRIPTION OF THE FIGURES

FIG. 4 is a side elevational view of the storage battery assembly configured as a portion of the one embodiment of the light polymerization device;

FIG. 5 is a side elevational view of the connection module of the one embodiment of the light polymerization device; and FIG. 6 is a side elevational view of a service adapter or module of the one embodiment of the light polymerization device.

DETAILED DESCRIPTION OF THE PREFERRED EMBODIMENTS

Figure 1:
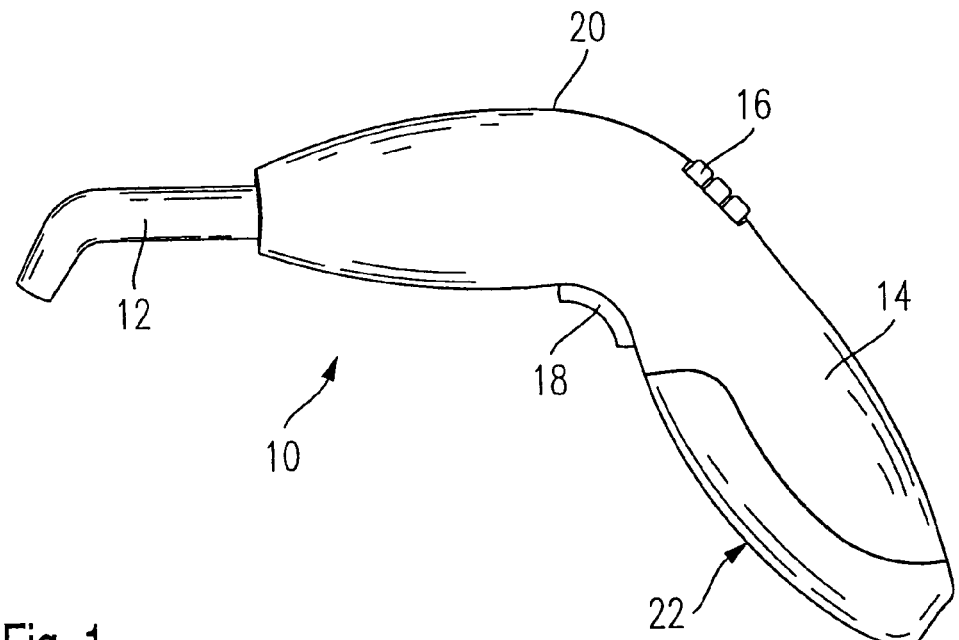
FIG. 1 is a side elevational view of a hand-held device portion of one embodiment of the light polymerization device of the present invention, the hand-held device incorporating a storage battery assembly.

The light polymerization device of this invention includes a plurality of modules including at least a base station module (30), a hand-held device module (10), a data/electrical connection module (24), a storage battery assembly module (22) securable to the hand-held device module (10), and a service module 62. A data bus (46) is provided between at least two of the modules via which data, in particular control data for the hand-held device (10), is transferable. The modules may be used in different pairings, or more than two may be used at the same time. FIG. 1 shows a portion of one embodiment of the light polymerization device of the present invention, the portion including a hand-held device 10 with a storage battery assembly or module 22. The hand-held device 10 comprises a conventionally known configuration substantially in a hand-held device shape. A light guide 12, which extends from the forward-end of the hand-held device 10, has its end bent in a conventional manner at an angle of 45°. A program selector switch 16 is mounted on the upper end of a hand grip 14 of the hand-held device as is, as well, if optionally provided, a display device for the display of operational information or other information concerning the condition of the hand-held device 10.

An actuation switch 18 is disposed opposite to the program selector switch 16; the actuation switch 18 is actuated in the manner of a trigger by, for example, the application of the index finger of the operator's hand thereagainst.

The hand-held device 10 comprises an angled housing 20 which, as can be seen in FIG. 1, has a rounded-off form such that it is user-friendly in connection with a hand-held operation. For example, the hand grip 14 has a basic overall spherical-type configuration. The actuation switch 18 extends adjacent the storage battery assembly 22, which ensures a harmonic outer shape of the hand grip 14 on its forward side. The storage battery assembly 22 is fixedly secured to the hand grip 14 by inwardly disposed seating tongues, which ensure that the storage battery assembly 22 does not come loose in the event of a hard set down landing of the hand-held device.

Both the electrical supply connection as well as a data bus extend into the interior between the storage battery assembly 22 and the hand-held device 10, as is described in more detail hereinafter.

Figure 2:
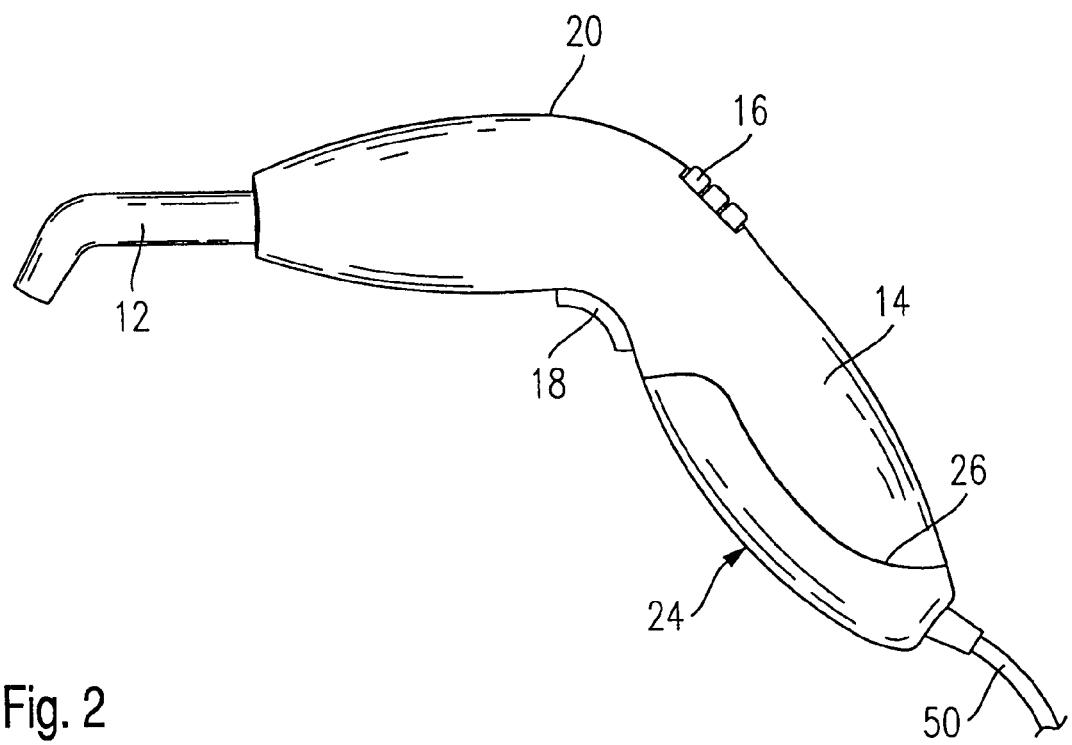
FIG. 2 is a side elevational view of a hand-held device portion of one embodiment of the light polymerization device of the present invention, the hand-held device incorporating a connection module.

The storage battery assembly 22 is releasably mounted on the handgrip 14. As seen in FIG. 2, the storage battery assembly 22 can be exchanged out for a data/electrical connection module 24, which has the same outer configuration. As is illustrated in FIGS. 1 and 2, the separation line 26 between the storage battery assembly 22 or, respectively, the data/electrical connection module 24, on the one hand, and the housing 20, on the other hand, extends not in a linear manner but in a wavy manner. This not only contributes to the aesthetically pleasing appearance of the device but, rather, makes possible an improved anchoring with relatively little construction effort.

Figure 3:
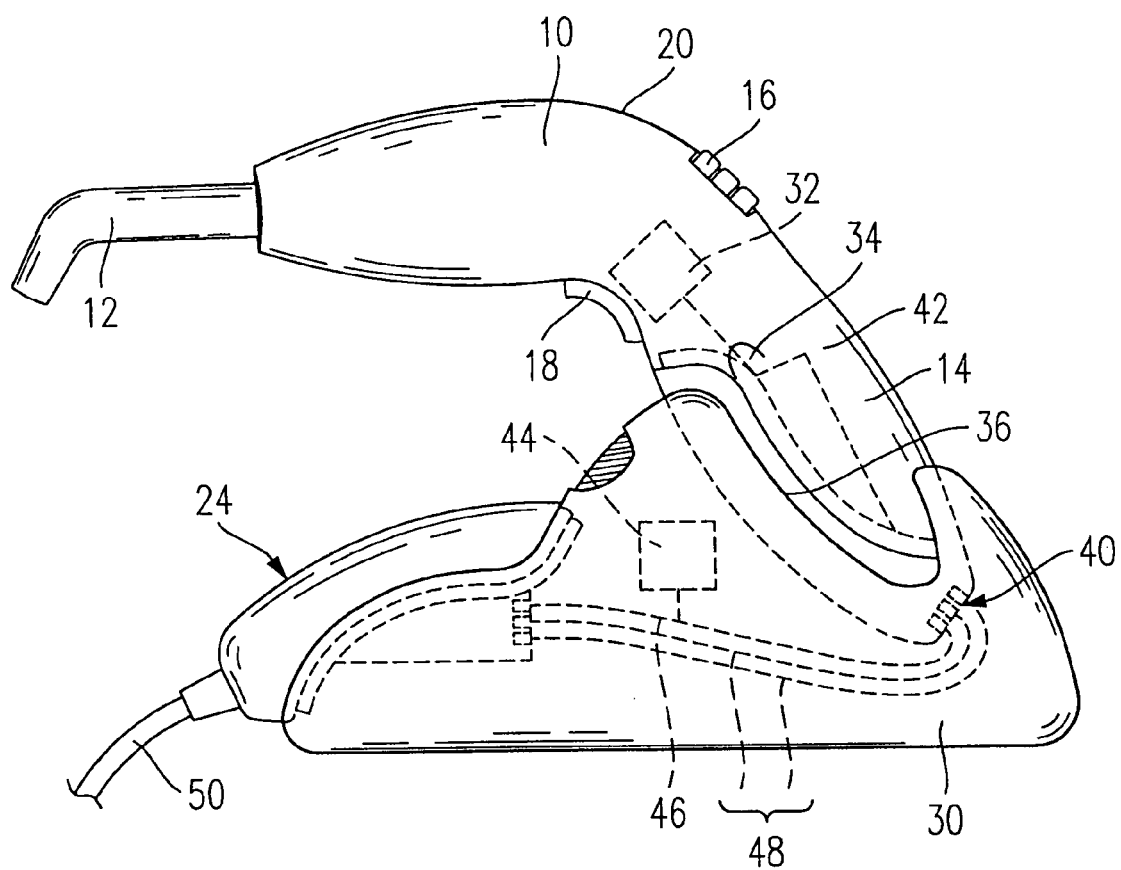
FIG. 3 is a side elevational view of the one embodiment of the light polymerization device shown in FIG. 1 and showing, as well, a base station, and the connection module connected to the base station.

As can be seen in FIG. 3, the hand-held device 10 can be inserted into a base station 30. The hand-held device 10 comprises a micro-controller 32 in, for example, the area between the actuation switch 18 and the program selector switch 16, which serves for controlling and calibrating the hand-held device and transmitting data relating to the important functions of the hand-held device. The hand-held device further comprises an interiorly disposed multiple socket or receptacle 34. The data bus port or interface as well as the releasably mounted electrical supply connectors are accessible via the receptacle 34. These three connectors are looped through module 36, which has been insertably mounted on the handgrip.

In the one embodiment of the light polymerization device of the present invention as shown in FIG. 3, the storage battery assembly 22 is deployed as a module. The storage battery assembly comprises a plug which cooperatively engages the receptacle 34, as well as a further micro-controller 38, which is shown in FIG. 4. At the lower end of the storage battery assembly, which, at the same time, forms the lower end of the handgrip 14, an additional receptacle is configured which is protected against impact. This receptacle provides electrical contact access between a corresponding plug 40 and a plurality of plug contacts of the base station 30, in the event that the hand-held device 10 is inserted into the base station 30. In this connection, the base station includes a receptacle 42, which permits only a single proper plug-in position of the hand-held device 10.

The base station 30 also comprises a micro-controller 44. The micro-controller 44 is, at the least, connected to a data bus 46, while the data bus 46 and the electrical supply connectors 48 are also looped through the base station 30.

The base station 30 comprises a further receptacle which is configured for the receipt of a module such as the storage battery assembly 22 or the data/electrical connection module 24.

In the illustrated embodiment, the data/electrical connection module 24 is inserted in this receptacle. Also here, as well, a multiple-branch receptacle is provided which is configured on the base station 30 and whose configuration corresponds to that of the receptacle 34 of the hand-held device.

One end of an electrical supply cable 50 is either releasably or fixedly connected to the opposed end of the connection adapter 24—that is, the respective end of the connection adapter 24 not inserted into the hand-held device— and the electrical supply cable 50 can be connected at its other end to a power pack which provides access to an electrical voltage of 12 or 24 volts which is to be conducted as the electrical energy supply to the base station and, consequently, to the hand-held device. This electrical supply cable 50 can, alternatively, be deployed to provide a direct supply of electrical energy from a power pack operation to the hand-held device, in the event that the data/electrical connection module 24 is disposed in the hand-held device.

A storage battery assembly 22 is illustrated in FIG. 4. The micro-controller 38 is connected, at the least, to the data bus 46, whereby it is to be understood that the electrical supply of the micro-controller 38 can be provided via supply connectors which extend to the micro-controller from the electrical supply connectors 48. The collective micro-controllers 38 comprise, in a conventional manner, either a non-volatile storage or a buffer battery which ensures the retention of data, in the event that the electrical supply from the exterior is no longer present. As can be seen in FIG. 4, a multiple-branch receptacle 54 is configured on the lower end of the storage battery assembly which permits the insertion of the plug 40 into the base station 30.

The outer configuration of the data/electrical connection module 24 corresponds to the outer configuration of the storage battery assembly 22. Surfaces which extend flush to the hand-held device are provided in the inserted disposition of the hand-held device so as to provide a grip-friendly operation of the hand-held device 10. The electrical supply cable 50 is connected with a plug power pack 60 so that a direct power pack operation of the hand-held device 10 via the inserted data/electrical connection module is possible but, as well, a charging of the storage battery assembly 22 in its inserted position as shown in FIG. 3 into the base station 30 is also possible.

It is to be understood that, in this disposition, a second storage battery assembly 22 can be inserted into the hand-held device 10 so that the hand-held device 10 can be placed into operation even while a second storage battery assembly 22 is being charged.

In the preferred embodiment, the hand-held device 10, the storage battery assembly 22, the data/electrical connection module 24, and the base station 30 each have one separated one-wire bus and a microcontroller which is connected to the one wire-bus. Both ends of the one-wire bus on the storage battery assembly 22 and the data/electrical connection module 24 have contact elements for the bus. In addition, one end of the one-wire bus on the hand-held device and the data/electrical connection module have contact elements for the bus. The contact element may be a plug or a socket. When, for example, the battery assembly 22 is inserted in the hand-held device 10, a contact of the one-wire bus of the battery is in electrical connection with the contact of the one-wire of the hand-held device. The same electrical connection is received between the battery assembly and the base station 30. As shown in FIG. 3, when the data/electrical connection module 24 is inserted in the base station 30, a contact of the one-wire bus of the data/electrical connection module is in electrical connection with the contact of the one-wire bus of the base station.

All of the devices 10, 22, 24, and 30 communicate with each other over the one-wire bus. Each device has its own fix address. There are no master and slave devices. Thus, each device can be master. The instruction code is built up in that way, and the first sign of the instruction code is identical with the address of the device. Thus the addressed device can send back the received address. If there is no answer the instruction code will be sent again for a defined time and when there is no answer from the device it will be assumed that the called device is not connected to the one-wire bus at the moment.

The further sign of the instruction code will be transferred to the device without an echo function. The instruction code ends with a "CR" (carriage return). An answer string of the called devices also end with a "CR".

If one of the devices will send something, it has first to proof if the one-wire bus was free for a defined time. During the transfer the device has to receive data and to proof if there is no bus collision. If there is a bus collision existing each device has to wait for a defined time, until it may starts again with a data transfer. Therefore the device with the longest waiting period has the lowest priority. The waiting periods are assigned fix to the devices.

A service module 62 (FIG. 6) can also be installed or inserted into the hand-held device 10 in lieu of the data/electrical connection module 24, the service module likewise offering a power pack electrical supply. In connection with the use of an additional service adapter or module 62, the hand-held device 10 can, when so configured, even be operated in a power pack operation. The service module 62, in addition to providing access to an electrical supply cable via a connection to a plug power pack 60, provides accessibility to a serial bus 64 for connection to a PC 66. In this manner, a data conversion is possible between the serial data bus 46 and a PC-compatible plug or receptacle 58 which includes a bus, such as a bus in accordance with the RS-232 standard, or the RS-422 standard, or other standards such as USB. The corresponding data conversion and a further micro-controller (not shown) are provided in the service module 62.

The service module 62 converts the one-wire bus into an RS-232 interface, (or other suitable interface such as a USB interface), which can be connected to a computer. On the RS-232 interface and on the one-wire bus standard 8-bit ASCII-Code is transferred. The RS-232 interface receives from the computer one string, if the string ends with a "CR". Each sign is sent back as an echo on the RS-232 interface. If the RS-232 has received the complete string, it will be transferred to the one-wire bus. If the transfer has done the prompt sign (>) is being sent on the RS-232. Only when the prompt sign was sent, can the computer send the next string. An answer from at least one device on the one-wire bus will be sent to the computer on the RS-232 interface. In principle the whole data transfer can be sent on the one-wire bus to the computer.

It is particularly advantageous that the data/electrical connection module 24, the storage battery assembly 22, and the service module 62 can comprise an outer configuration which, upon insertion of the respective module into or on the hand-held device, extends in a flush manner with the surface of the hand-held device. In this manner, an ergonomic hand-held capability is ensured in spite of the relatively small construction size of the light polymerization device.

It is to be understood that the inventive configuration can offer numerous combination possibilities for making available the service function of the hand-held device.

The important feature offered by the inventive arrangement is the transmission of the respective relevant data via the data bus, and, in fact, the transmission of such data independent from the plugged-in condition and the order of the plugging-in of components. The synchronization of data can be effected in accordance with the respective inserted condition between two modules and, as well a calibration of the hand-held device in a desired manner via the use of the service adapter 62 is possible. It is also to be understood that the hand-held device 10, once it has been placed into calibrated condition, is self-sufficient so that, for example, it is not necessary for each dental practice to have available a service module 62. However, focused and detailed information can be provided for evaluating a degradation of the light output performance as well as evaluating a reduction of the capacity of a storage battery assembly in the course of its operational life and the required measures can then automatically be implemented based upon such evaluations.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. Light polymerization apparatus comprising:
   a hand-held module (10) for the light polymerization of dental materials, the hand held module being provided with a handgrip (14);
   at least two or more additional modules that are structurally connectable for assembly with the handheld module, the additional modules including a base station module (30), a data/electrical connection module (24), a service module (62), and a storage battery module (22); and
   a data bus (46) and electrical connections (48) provided between at least two modules (10, 22; 10, 24; 10, 62; 22, 30; 30, 24; 30, 62) via which data, in particular control data for the hand-held module (10), is transferable.

2. A light polymerization apparatus according to claim 1, wherein at least one of the hand-held module (10), the storage battery module (22), the base station module (30), and the service module (62) includes at least one port or interface for the data bus (46), which is additional to, and especially, adjacent to, the plurality of electrical power supply connectors (48) provided for the supply of electrical energy.

3. A light polymerization apparatus according to claim 1, wherein at least one port for the data bus (46) and at least two electrical power supply connectors (48) are configured in the respective form of a multi-pin plug and a multiple-branch receptacle (54).

4. A light polymerization apparatus according to claim 1, wherein the data bus (46) is mounted between the storage battery module (22) and a selected one of the hand-held module (10), the base station module (30), and the storage battery module (22).

5. A light polymerization apparatus according to claim 1, wherein the data/electrical connection module (24) is connected with an external electrical power supply source, and the data/electrical connection module (24) is connectable with at least one of the hand-held module (10) and the base station module (30).

6. A light polymerization apparatus according to claim 5, wherein, in connection with a power pack operation of the hand-held module (10), the data/electrical connection module (24) is integrated into the hand-held module (10), and the data/electrical connection module (24) conducts electrical power supply energy supplied via an electrical power supply cable (50) to the hand-held module (10).

7. A light polymerization apparatus according to claim 1, and further comprising a service module (62) connected, in particular, with both a computer (66) and, via a power pack (60), with an external energy source, the service module (62) being connectable with at least one of the hand-held module (10) arid the base station module (30) such that at least one of an adjustment of the hand-held module (10) into its operational condition, a calibration of the hand-held module (10), and a transmission of data stored in a computer (66) to at least one of the hand-held module (10), the storage battery module (22), and the base station module (30) can be effected.

8. A light polymerization apparatus according to claim 5, wherein the data/electrical connection module (24), the storage battery module (22), and the service module (62) have an outer configuration which extends flush with a surface of the hand-held module (10), the separation line (26) between the hand-held module (10) and the other modules extends not in a linear manner but in a wavy manner to contribute to the aesthetically pleasing appearance of the apparatus and makes possible an improved anchoring with relatively little construction effort.

9. A light polymerization apparatus according to claim 5, wherein the data/electrical connection module (24) and a service module (62) connected with an external energy source each comprise a housing having an interface, the form of the housing and its interface being compatible with the housing of the storage battery module (22).

10. A light polymerization apparatus according to claim 5, wherein a selected one of the housing of the storage battery module (22), the data/electrical connection module (24), and a service module (62) connected with an external energy source forms a portion of the handgrip (14) of the hand-held module (10).

11. A light polymerization apparatus according to claim 1, wherein the hand held module is provided with a microcontroller (32), and wherein at least one of calibration data, light output performance data, mass data, and operational time data of the light polymerization apparatus are stored in the microcontroller.

12. A light polymerization apparatus according to claim 1, wherein the storage battery module (22) is releasably securable to the hand-held module (10) and control data for the hand-held module (10) are transferable via the data bus (46).

13. A light polymerization apparatus according to claim 5, wherein the data/electrical connection module (24) is connected with an external electrical power supply source via a power pack (60) and the data/electrical connection module (24) is connectable with at least one of the hand-held module (10) and the base station module (30) via one of a multi-pin plug and a multi-branch receptacle (54).

14. A light polymerization apparatus according to claim 6, wherein the data/electrical connection module (24) is integrated into the handgrip (14) of the hand-held module (10).

15. A light polymerization apparatus according to claim 1, wherein at least one of the hand-held module (10), the base station module (30), and the storage battery module (22) includes a micro-controller (38, 44).

16. A light polymerization apparatus according to claim 11, wherein the respective calibration data, light output performance data, mass data, and operational time data of the light polymerization apparatus are stored in at least the hand-held module (10) and are stored as well in the base station module (30) following a reading thereof via the data bus (46).

* * * * *